(12) United States Patent
Hatta et al.

(10) Patent No.: US 10,357,584 B2
(45) Date of Patent: Jul. 23, 2019

(54) CUBICLE UNIT, TRANSPORTATION VEHICLE, AND ILLUMINATION CONTROL METHOD

(71) Applicant: Panasonic Intellectual Property Management Co., Ltd., Osaka (JP)

(72) Inventors: Kazuhiro Hatta, Osaka (JP); Junichi Hasegawa, Osaka (JP); Kiyotaka Hirata, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 212 days.

(21) Appl. No.: 15/486,100

(22) Filed: Apr. 12, 2017

(65) Prior Publication Data

US 2017/0296687 A1    Oct. 19, 2017

(30) Foreign Application Priority Data

Apr. 18, 2016  (JP) .................. 2016-083177

(51) Int. Cl.
| | |
|---|---|
| *A47K 4/00* | (2006.01) |
| *A61L 2/10* | (2006.01) |
| *B64D 11/02* | (2006.01) |
| *H05B 33/08* | (2006.01) |
| *H05B 37/02* | (2006.01) |
| *B64D 11/00* | (2006.01) |

(52) U.S. Cl.
CPC .............. *A61L 2/10* (2013.01); *B64D 11/02* (2013.01); *H05B 33/0854* (2013.01); *H05B 33/0872* (2013.01); *H05B 37/0218* (2013.01); *H05B 37/0227* (2013.01); *H05B 37/0281* (2013.01); *B64D 2011/0038* (2013.01); *Y02B 20/42* (2013.01); *Y02B 20/46* (2013.01)

(58) Field of Classification Search
None
See application file for complete search history.

(56) References Cited

U.S. PATENT DOCUMENTS

| | | | |
|---|---|---|---|
| 6,231,203 B1 * | 5/2001 | Olshausen | F21S 8/035 362/101 |
| 10,194,777 B2 * | 2/2019 | Laundre | A47K 13/24 |
| 2004/0090787 A1 * | 5/2004 | Dowling | H05B 33/0842 362/464 |

(Continued)

FOREIGN PATENT DOCUMENTS

| | | |
|---|---|---|
| JP | 2000-260580 A | 9/2000 |
| JP | 2000-294387 A | 10/2000 |

(Continued)

*Primary Examiner* — Andrew J Coughlin
(74) *Attorney, Agent, or Firm* — Renner, Otto, Boisselle & Sklar, LLP

(57) ABSTRACT

A cubicle unit includes a first illumination apparatus, a second illumination apparatus, a sensor, and a controller. When a brightness sensed by the sensor is a predetermined brightness or less, the controller causes the second illumination apparatus to emit light having a first color temperature lower than a color temperature of light emitted by the first illumination apparatus. When the brightness sensed by the sensor is greater than the predetermined brightness, the controller causes the second illumination apparatus to emit light having a second color temperature lower than the first color temperature.

11 Claims, 12 Drawing Sheets

(56) References Cited

U.S. PATENT DOCUMENTS

| | | | |
|---|---|---|---|
| 2005/0103935 A1 | 5/2005 | Sprenger et al. | |
| 2007/0153514 A1 | 7/2007 | Dowling et al. | |
| 2012/0068613 A1* | 3/2012 | Veneto | A47K 13/24 315/159 |
| 2014/0022775 A1* | 1/2014 | Bostic | F21L 4/00 362/191 |
| 2018/0116470 A1* | 5/2018 | Szemetylo | E03C 1/0408 |

FOREIGN PATENT DOCUMENTS

| | | |
|---|---|---|
| JP | 2005-067600 A | 3/2005 |
| JP | 2005-537613 A | 12/2005 |
| JP | 2015-002832 A | 1/2015 |

* cited by examiner

CUBICLE UNIT, TRANSPORTATION VEHICLE, AND ILLUMINATION CONTROL METHOD

CROSS REFERENCE TO RELATED APPLICATION

This application claims the benefit of priority of Japanese Patent Application Number 2016-083177 filed on Apr. 18, 2016, the entire content of which is hereby incorporated by reference.

BACKGROUND

1. Technical Field

The present disclosure relates to illumination control of a cubicle unit provided in a transportation vehicle, for example.

2. Description of the Related Art

Conventionally, an illumination apparatus for use in an aircraft is known. For example, Japanese Unexamined Patent Application Publication No. 2005-537613 (PTL 1) discloses a system which illuminates the interior of an aircraft with white light and non-white light.

SUMMARY

During a long-haul flight, an aircraft may provide a time slot during which illumination in a cabin is dimmed for passengers to sleep. If a passenger still drowsy goes to a restroom while the illumination in the cabin is dimmed, the passenger may be fully woke up (fully awakened) by the illumination in the restroom.

The present disclosure provides a cubicle unit, a transportation vehicle, and an illumination control method which can inhibit a user from being fully awakened unnecessarily.

A cubicle unit according to one aspect of the present disclosure includes: sidewalls, ceiling, and flooring which form a cubicle; a toilet pan placed in the cubicle; a first illumination apparatus which emits light to illuminate an interior of the cubicle, the first illumination apparatus being placed on the ceiling or one of the sidewalls; a second illumination apparatus which emits light to illuminate a floor surface of the cubicle, the floor surface being part of the flooring, the second illumination apparatus being placed at a position lower than a top end of the toilet pan in the cubicle; a sensor which senses a brightness outside the cubicle; and a controller which (i) causes, when the brightness sensed by the sensor is a predetermined brightness or less, the second illumination apparatus to emit light having a first color temperature lower than a color temperature of light emitted by the first illumination apparatus, and (ii) causes, when the brightness sensed by the sensor is greater than the predetermined brightness, the second illumination apparatus to emit light having a second color temperature higher than the first color temperature.

A transportation vehicle according to one aspect of the present disclosure includes the cubicle unit.

An illumination control method according to one aspect of the present disclosure is a method for controlling illumination in a cubicle unit including: sidewalls, ceiling, and flooring which form a cubicle; a toilet pan placed in the cubicle; a first illumination apparatus which emits light to illuminate an interior of the cubicle, the first illumination apparatus being placed on the ceiling or one of the sidewalls; and a second illumination apparatus which emits light to illuminate a floor surface of the cubicle, the floor surface being part of the flooring, the second illumination apparatus being placed at a position lower than a top end of the toilet pan in the cubicle, the method including: sensing a brightness outside the cubicle; causing, when the brightness sensed is a predetermined brightness or less, the second illumination apparatus to emit light having a first color temperature lower than a color temperature of light emitted by the first illumination apparatus; and causing, when the brightness sensed is greater than the predetermined brightness, the second illumination apparatus to emit light having a second color temperature higher than the first color temperature.

According to the cubicle unit, the transportation vehicle, and the illumination control method of the present disclosure, a user can be inhibited from being fully awakened unnecessarily.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENTS

Hereinafter, embodiments of the present disclosure are to be described, with reference to the accompanying drawings. The embodiments described below are each generic and specific illustration. Values, shapes, materials, components, and arrangement and connection between the components, steps, and the order of the steps shown in the following embodiments are merely one example and not intended to limit the present disclosure. Among the components in the embodiments below, components not recited in any one of the independent claims defining the most generic part of the inventive concept of the present disclosure are described as arbitrary components.

The figures are schematic views and do not necessarily illustrate the present disclosure precisely. In the figures, the reference sign is used to refer to substantially the same configuration, and duplicate description may be omitted or simplified.

Embodiment

[Configuration]

Figure 1A:
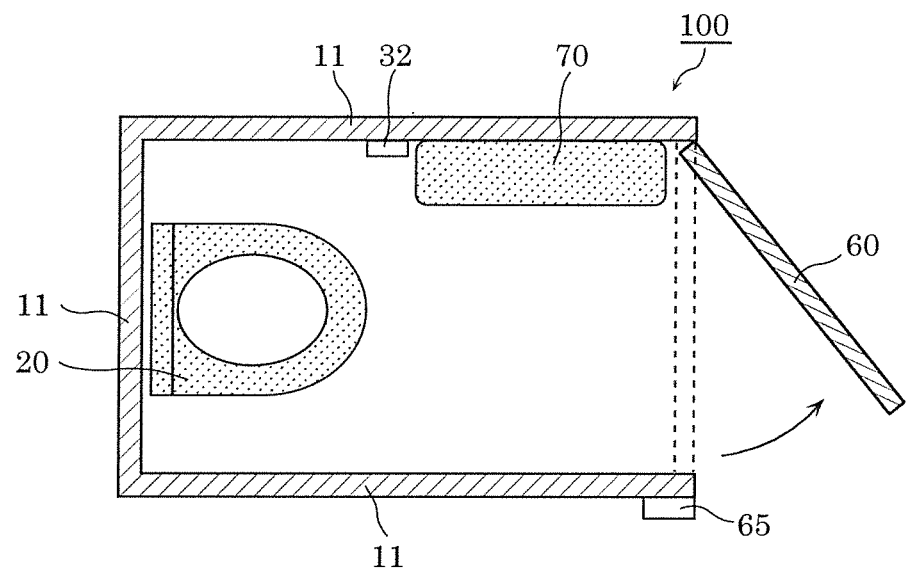
FIG. 1A is a diagram illustrating an internal construction of a cubicle unit according to an embodiment when viewed from the top.
Figure 1B:
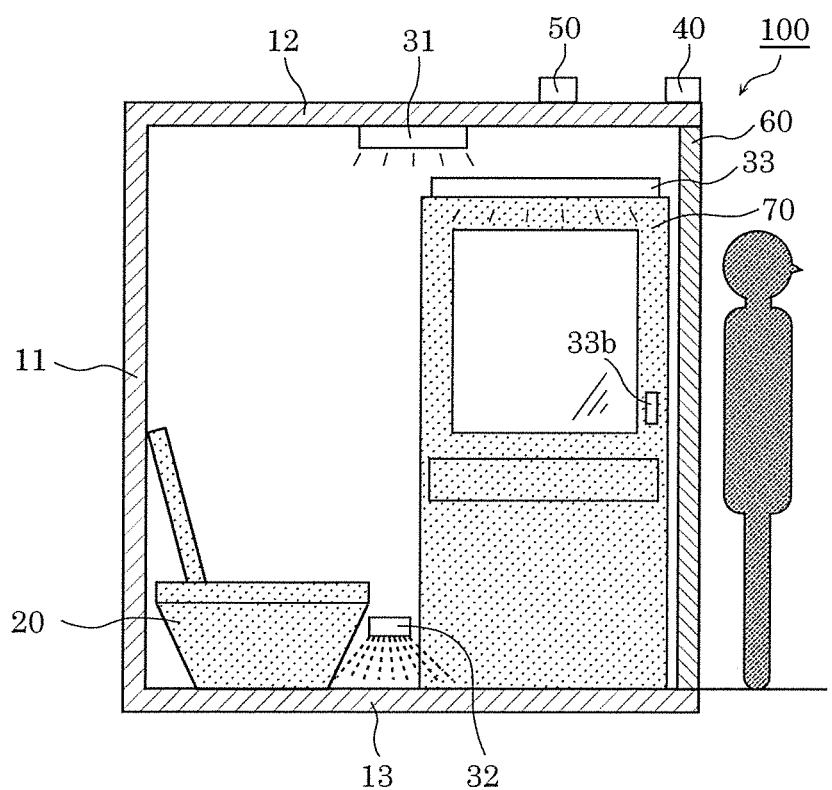
FIG. 1B is a diagram illustrating the internal construction of the cubicle unit according to the embodiment when viewed from the side.
Figure 2:
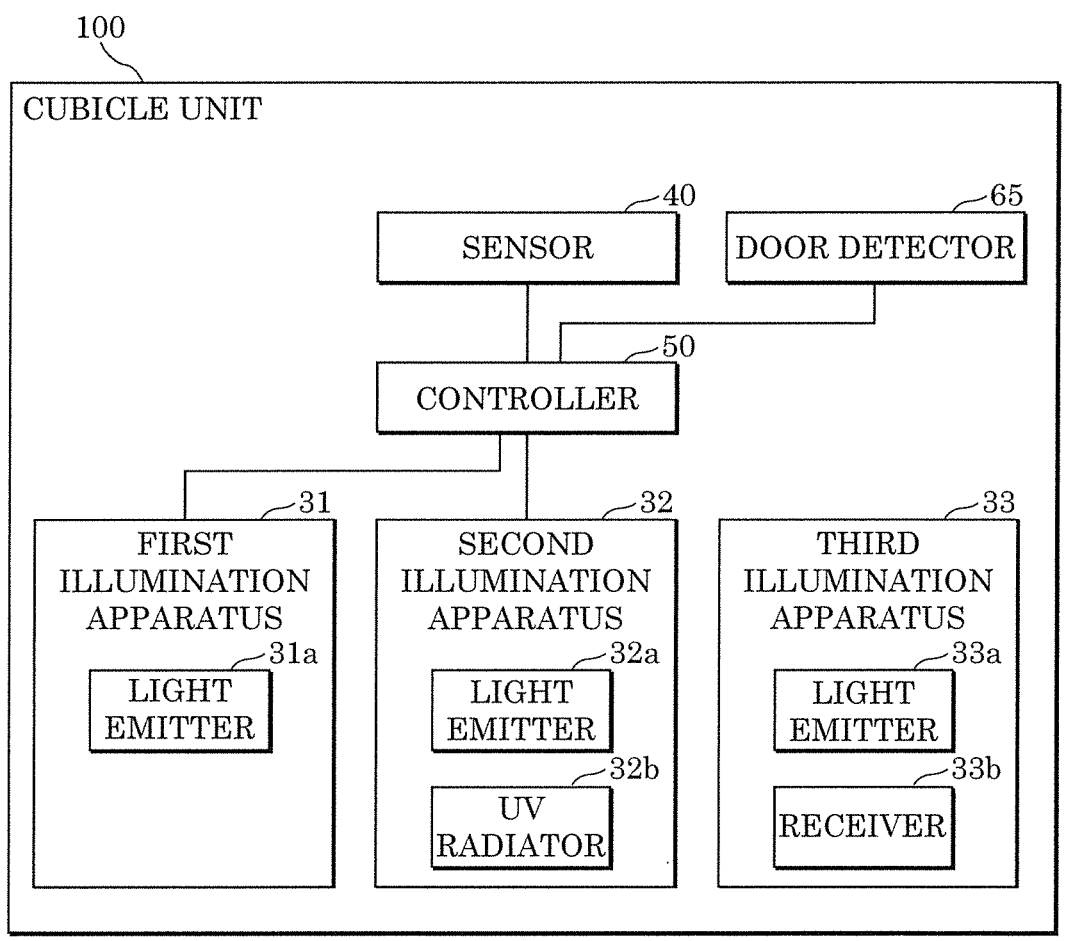
FIG. 2 is a block diagram of a functional configuration of the cubicle unit according to the embodiment.

Initially, a configuration of a cubicle unit according to an embodiment of the present disclosure is described. FIG. 1A is a diagram illustrating an internal construction of the cubicle unit according to the embodiment when viewed from the top. FIG. 1B is a diagram illustrating the internal construction of the cubicle unit according to the embodiment when viewed from the side. FIG. 2 is a block diagram of a functional configuration of the cubicle unit according to the embodiment.

As illustrated in FIGS. 1A, 1B, and 2, cubicle unit 100 according to the embodiment is a toilet unit placed in a transportation vehicle such as an aircraft. Cubicle unit 100 is, typically, placed indoors. Cubicle unit 100 may be placed inside a building, for example.

Cubicle unit 100 includes sidewalls 11, ceiling 12, and flooring 13 which form a cubicle, and toilet pan 20, first illumination apparatus 31, second illumination apparatus 32, third illumination apparatus 33, sensor 40, controller 50, door 60, door detector 65, and basin 70.

Sidewalls 11, ceiling 12, and flooring 13 are rectangular board members. Sidewalls 11, ceiling 12, and flooring 13 form the cubicle in a generally rectangular parallelepiped shape. The cubicle is, specifically, a space that is enclosed by wall surfaces of sidewalls 11, a ceiling surface of ceiling 12, and a floor surface of flooring 13.

Sidewalls 11, ceiling 12, and flooring 13 are formed of resin such as polyethylene resin or fiber reinforced plastics (FRP), for example, but they may be formed of metal and are not particularly limited.

Door 60 is for allowing a user to enter and exit the cubicle and is lockable from inside the cubicle by the user. Door 60 is a rectangular board member. Door 60 is formed of resin such as polyethylene resin or FRP, for example. However, door 60 may be formed of metal and is not particularly limited.

Door detector 65 is an example of a lock detector and detects whether door 60 is locked or not. Door detector 65, for example, includes a sensor which structurally or optically detects whether a mechanism for locking door 60 is functioning. Moreover, door detector 65, for example, outputs a first digital signal as a detection result. The first digital signal is high when door 60 is locked, and low when door 60 is not locked. Note that the logic of the first digital signal may be inverted.

Moreover, door detector 65 is also an example of an opening and closing detector, and detects opening and closing of door 60. Door detector 65, for example, includes a door sensor which detects the opening and closing of door 60 using infrared. However, door detector 65 may detect the opening and closing of door 60, using another sensor. Door detector 65, for example, outputs a second digital signal as a detection result. The second digital signal is high when door 60 is open, and low when door 60 is closed. Note that the logic of the second digital signal may be inverted.

Door detector 65 is placed on sidewall 11 (the outside of sidewall 11), for example, but is not particularly limited.

Toilet pan 20 is a sanitary fixture for the user to use the toilet. Toilet pan 20 is placed in the cubicle. Toilet pan 20 is formed of ceramic or resin. Toilet pan 20 may be a western toilet or may be a squat toilet. The washing system of toilet pan 20 may be a flushing system (circuit system) or may be a vacuum system. A specific embodiment of toilet pan 20 is not particularly limited.

First illumination apparatus 31 is placed on sidewall 11 or ceiling 12. First illumination apparatus 31 is, what is called, a main lighting (direct lighting) and illuminates the entirety of the interior of the cubicle by emitting light. First illumination apparatus 31 is, for example, a downlight embedded in ceiling 12. However, first illumination apparatus 31 may be any other illumination apparatus, such as a spotlight, that can be attached to a ceiling surface, which is part of (bottom surface) of ceiling 12, or an inner wall surface which is part of sidewalls 11. First illumination apparatus 31 may also be a line illumination apparatus if it is placed on sidewall 11 (inner wall surface). Light emission of first illumination apparatus 31 is controlled by controller 50, independently of second illumination apparatus 32. First illumination apparatus 31, specifically, includes light emitter 31a.

Light emitter 31a is, for example, a light emitting module using a light emitting diode (LED) as a light emitting element. Light emitter 31a emits white light. Intensity of light emitted by light emitter 31a is controllable by controller 50 (brightness control).

A color temperature of the white light emitted by light emitter 31a is 5000 K, for example, but is not particularly limited. In the present embodiment, light emitter 31a is a light emitting module the color control of which is not allowed. Alternatively, light emitter 31a may be a light emitting module the color control of which is allowed.

Second illumination apparatus 32 is placed at a position lower than the top end of toilet pan 20 in the cubicle. Note that the top end of toilet pan 20, if toilet pan 20 includes a lid, means the top end (top end of the lid) when the lid is open. Second illumination apparatus 32 is, what is called, a sub lighting (indirect lighting) and illuminates a floor surface of the cubicle by emitting light, the floor surface being part (top surface) of flooring 13. Light emission of second illumination apparatus 32 is controlled by controller 50, independently of first illumination apparatus 31. Second illumination apparatus 32, specifically, includes light emitter 32a and UV radiator 32b.

Light emitter 32a is, for example, a light emitting module using an LED as a light emitting element. Light emitter 32a emits white light. Light emitter 32a is a light emitting module which includes light sources which emit light having different emission colors (color temperatures), and the dimming control and color control (emission color control) of which are allowed. Note that light emitter 32a may emit light having a first color temperature and light having a second color temperature described below, and stepless color control is not essential.

UV (ultraviolet) emitter 32b emits ultraviolet radiation. UV radiator 32b is configured of, for example, an ultraviolet LED or an ultraviolet lamp. Ultraviolet radiation is used to disinfect (sterilize) the interior of the cubicle, for example. Note that UV radiator 32b may be implemented in a separate radiation apparatus from second illumination apparatus 32.

Third illumination apparatus 33 is a work illumination apparatus which is placed above basin 70 and illuminates a user of basin 70 by emitting light. Light emission of third illumination apparatus 33 is controlled independently of first illumination apparatus 31 and second illumination apparatus 32. This allows the user to freely use third illumination apparatus 33, irrespective of the illumination statuses of first illumination apparatus 31 and second illumination apparatus 32. Light emission of third illumination apparatus 33 is controlled by, for example, a controller (not shown) included in third illumination apparatus 33, but may be controlled by controller 50.

Third illumination apparatus 33 may have a color rendering property (color rendering index: CRI) higher than first illumination apparatus 31. This can provide the user of basin 70 with high color reproduction. Third illumination apparatus 33 which has a high color rendering property is suited for a user who puts on makeup using basin 70. Third illumination apparatus 33, specifically, includes light emitter 33a and receiver 33b.

Light emitter 33a is, for example, a light emitting module using an LED as a light emitting element. Light emitter 33a emits white light. Light emitter 33a includes light sources which emit light having different emission colors (color temperatures) and is configured to emit light in (at least two) illumination modes.

Receiver 33b receives, from a user, an indication of turning on and off of third illumination apparatus 33, and a selection from among the illumination modes of third illumination apparatus 33. Receiver 33b is, specifically, a user interface such as a touch panel or a push button. Receiver 33b allows the user to select an illumination mode of third illumination apparatus 33.

The illumination modes include a first illumination mode and a second illumination mode, for example. In the first illumination mode, the emission color is optimized for the user to put on makeup for business purposes. In the second illumination mode, the emission color is optimized for the user to put on makeup for private. This allows the user of basin 70 to enjoy makeup as intended, depending on a scene.

Basin 70 is a vanity used by the user to put on makeup and wash hands, for example. Basin 70 includes a wash basin and a mirror.

Sensor 40 senses a brightness outside the cubicle (cubicle unit 100). Sensor 40, more specifically, senses the brightness outside the cubicle which is also a brightness inside a transportation vehicle (the cabin in the case where the transportation vehicle is an aircraft). In other words, sensor 40 senses a brightness indoors (in a building or transportation vehicle), rather than outdoors.

Sensor 40, for example, includes an imaging unit which includes a complementary metal oxide semiconductor (CMOS) sensor or an RGB sensor, and senses the brightness by capturing an image outside the cubicle. Sensor 40 may include an illuminance sensor or the like and sense the brightness by the illuminance sensor. Sensor 40 is placed on ceiling 12, for example, but the placement of sensor 40 is not particularly limited. Sensor 40 may be placed away from the cubicle.

Sensor 40 may also indirectly sense the brightness outside the cubicle, rather than directly sensing it. For example, sensor 40 may obtain (monitor) a pulse width modulation (PWM) signal which controls a brightness of an illumination apparatus outside the cubicle, or a current value or the like through the illumination apparatus outside the cubicle, and indirectly sense the brightness outside the cubicle based on the obtained information.

Moreover, sensor 40, for example, outputs current or voltage according to the brightness sensed, as a result of the sensing. Sensor 40 may be configured of, for example, a processor, a microcomputer, or a dedicated circuit, in addition to the sensors mentioned above.

Controller 50 is a control apparatus which controls light emission of first illumination apparatus 31 and second illumination apparatus 32. Controller 50 may further control light emission of third illumination apparatus 33. Controller 50 is placed on ceiling 12, for example, but the placement of controller 50 is not particularly limited.

Controller 50 is implemented in, specifically, a processor, a microcomputer, or a dedicated circuit, for example. Controller 50 may also be implemented in a combination of a processor, a microcomputer, and a dedicated circuit.

[Common Problems with Illumination Control]

Next, common problems with illumination control are described. For example, illumination control which switches between illumination modes, based on whether a user is in the cubicle, is considered. Controller 50 determines that a person is present in the cubicle if, for example, door detector 65 detects that door 60 is locked. In this case, controller 50 causes first illumination apparatus 31 and second illumination apparatus 32 to emit bright light (full on).

On the other hand, controller 50 determines that no one is present in the cubicle if, for example, door detector 65 determines that door 60 is not locked. In this case, controller 50 causes first illumination apparatus 31 to emit dim light and turns off second illumination apparatus 32.

Common problems with such illumination control are as follows. For example, when the interior of the cubicle is bright and outside the cubicle is relatively dim, it takes time for the user moved out of the cubicle to adapt to the dark environment outside the cubicle. In that case, the user has to move around while having an impression of the environment being dark. There is thus a risk that the user falls down or causes a collision. In addition, when outside the cubicle is relatively dim, if the user enters the cubicle and is exposed to bright light, the user may fully wake up unnecessarily.

[Details of Illumination Control]

Figure 3:
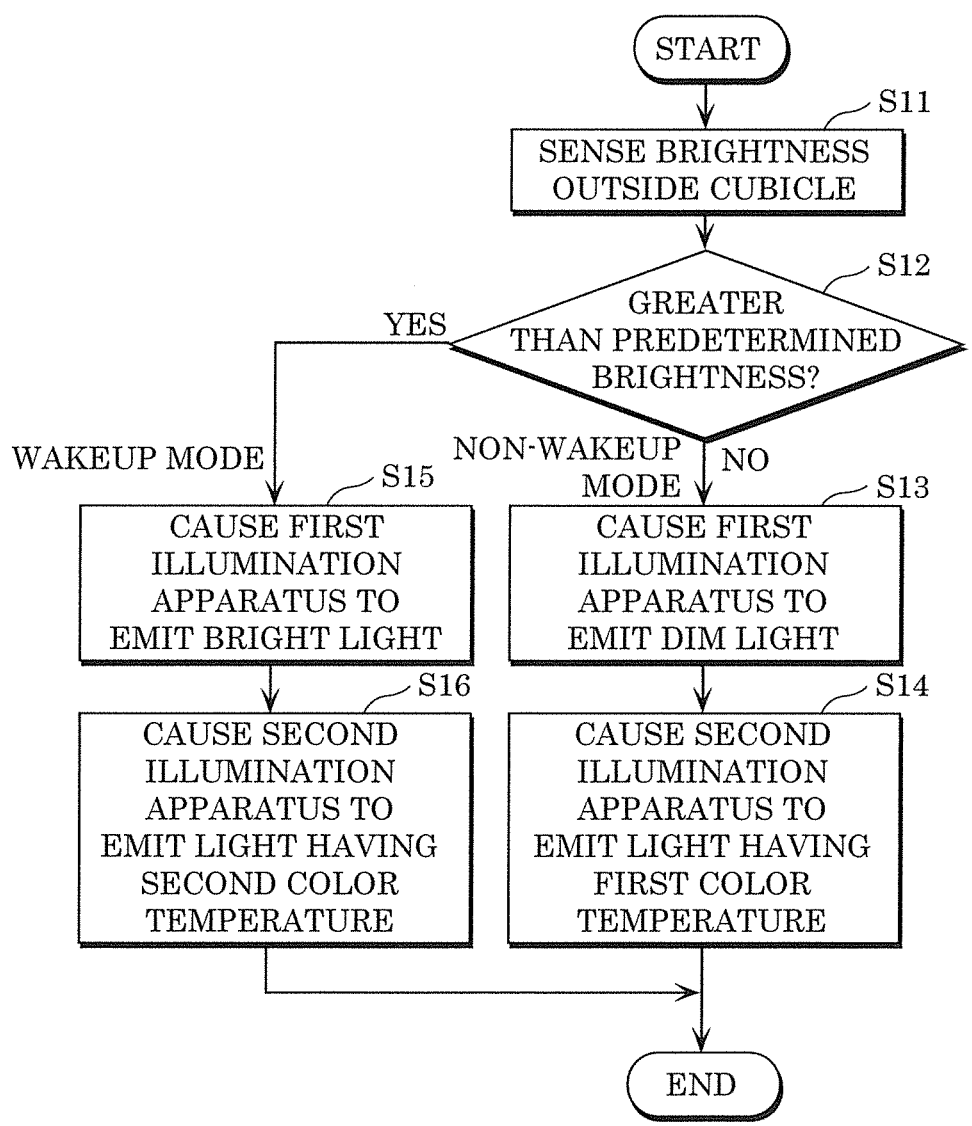
FIG. 3 is a flowchart of light-emission control of switching between illumination modes according to a brightness outside the cubicle.

Thus, controller 50 performs control (illumination control) of switching between illumination modes, according to a brightness outside the cubicle. FIG. 3 is a flowchart of the illumination control.

Sensor 40 senses a brightness outside the cubicle (S11). Controller 50 determines whether the brightness sensed by sensor 40 is brighter than a predetermined brightness (S12). Controller 50, specifically, determines whether a value of voltage or current output from sensor 40 indicates that the brightness sensed by sensor 40 is brighter than the predetermined brightness. Sensor 40 may carry out such determination. Note that the predetermined brightness may be empirically and experimentally determined as a threshold for switching between illumination modes, as appropriate.

Figure 4A:
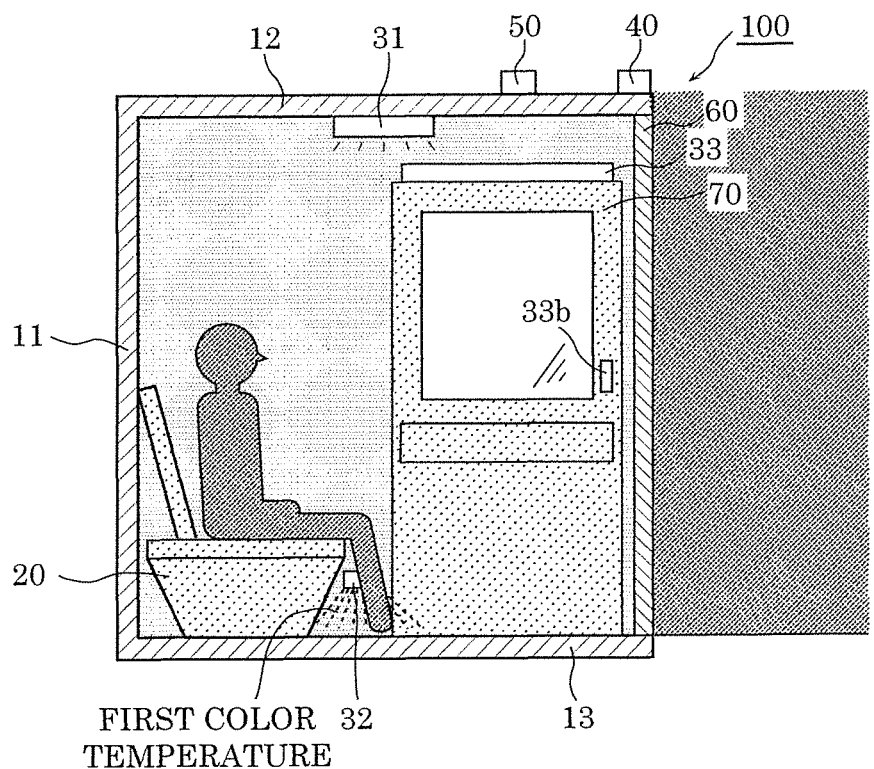
FIG. 4A is a schematic view of non-wakeup mode illumination control.

In step S12, if the brightness sensed by sensor 40 is determined to be the predetermined brightness or less (No in S12), it is estimated that outside of the cubicle is dimmed for the user to go to sleep. Thus, controller 50 performs non-wakeup mode illumination control for reducing the wakefulness of the user. FIG. 4A is a schematic view of the non-wakeup mode illumination control.

As illustrated in FIG. 4A, in the non-wakeup mode illumination control (hereinafter, also simply referred to as a non-wakeup mode), controller 50, specifically, causes first illumination apparatus 31 to emit light dimmer than in wakeup mode illumination control (hereinafter, also simply referred to as a wakeup mode) (S13). In other words, if the brightness sensed by sensor 40 is the predetermined brightness or less, controller 50 causes first illumination apparatus 31 to emit light dimmer than when the brightness sensed by sensor 40 is greater than the predetermined brightness.

Then, controller 50 causes second illumination apparatus 32 to emit light having the first color temperature lower than a color temperature of light emitted by first illumination apparatus 31 (S14). The first color temperature is, for example, 3000 K, but may be any color temperature that is lower than the color temperature of light emitted by first illumination apparatus 31.

Note that if the color produced by first illumination apparatus 31 is controllable, the first color temperature may be lower than the color temperature of light that is emitted by first illumination apparatus 31 during the non-wakeup mode. Moreover, in such a case, the first color temperature may be lower than a defined color temperature of first illumination apparatus 31. For example, if the color produced by first illumination apparatus 31 is controlled in a color temperature range of 3000 K or greater and 5000 K or less, the defined color temperature may be 4000 K which is an intermediate value, 5000 K which is a maximum value, or 3000 K which is a minimum value.

Figure 4B:
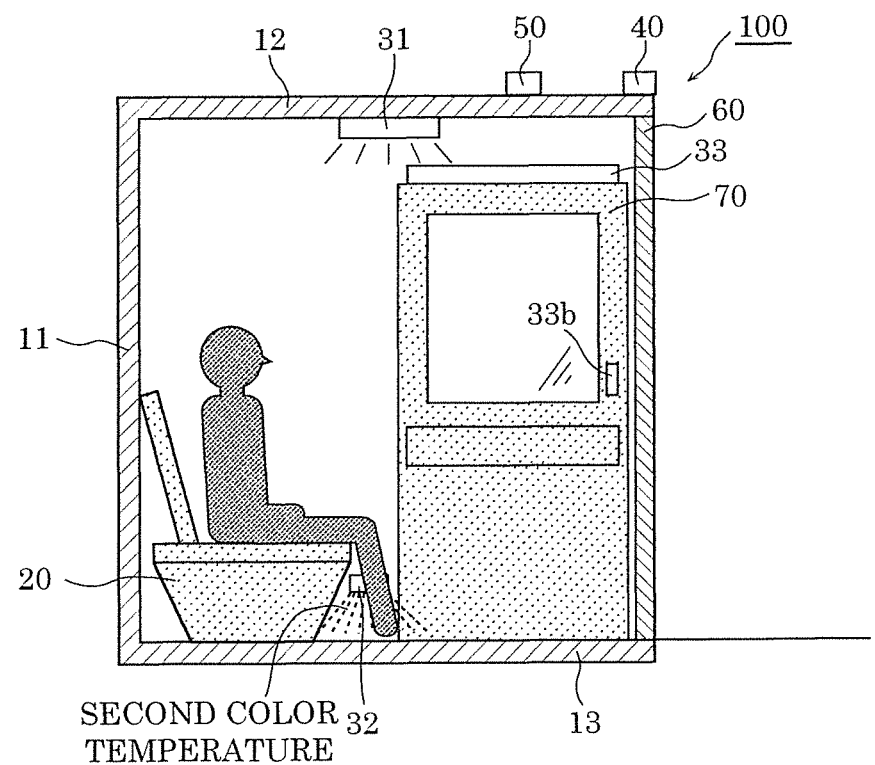
FIG. 4B is a schematic view of wakeup mode illumination control.

On the other hand, if controller 50 determines that the brightness sensed by sensor 40 is brighter than the predetermined brightness in step S12 (Yes in S12), it is contemplated that there is no need to inhibit an increase of the wakefulness of the user, rather, that the wakefulness of the user may better be increased. For this reason, controller 50 performs the wakeup mode illumination control for inhibiting a reduction of the wakefulness of the user. FIG. 4B is a schematic view of the illumination control in the wakeup mode.

As illustrated in FIG. 4B, in the wakeup mode, controller 50, specifically, causes first illumination apparatus 31 to emit light brighter than in the non-wakeup mode (S15). Stated differently, controller 50 increases light output of first illumination apparatus 31 greater than in the non-wakeup mode. Then, controller 50 causes second illumination apparatus 32 to emit light having the second color temperature greater than the first color temperature (S16). The second color temperature is, for example, 5000 K, but may be any color temperature greater than the first color temperature.

[Effects]

Figure 5:
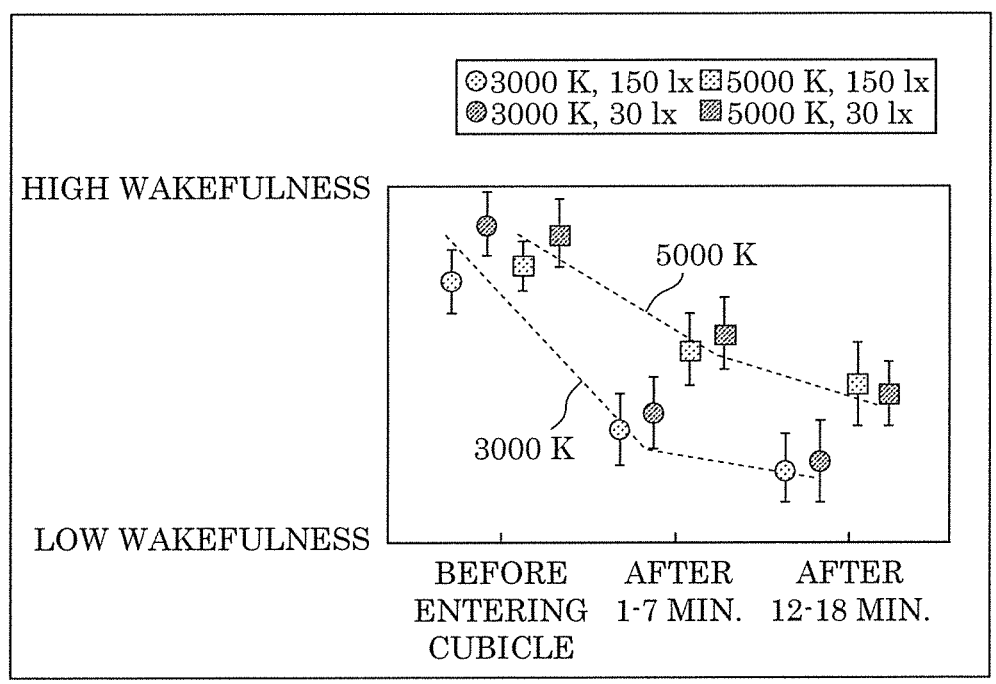
FIG. 5 is a diagram for illustrating effects gained by controlling a color temperature.

The color temperature of light emitted by second illumination apparatus 32 in the non-wakeup mode is lower than the color temperature of light emitted by first illumination apparatus 31 in the wakeup mode. Advantageous effects gained by such color temperature control are now described. FIG. 5 is a diagram for illustrating the effects gained by controlling the color temperature.

FIG. 5 shows plots of averages of the wakefulness of eight test subjects measured before and after entry into the cubicle. In FIG. 5, maximum values and minimum values are plotted, in addition to the averages. The wakefulness is indicated on the vertical axis and time is indicated on the horizontal axis in FIG. 5. Wakefulness of the test subjects are measured when the color temperature of the illumination in the cubicle is 3000 K and 5000 K. Wakefulness of the test subjects are also measured when illuminance of the illumination in the cubicle is 30 lx and 150 lx. Note that the wakefulness depends on a center frequency of brainwaves of each test subject, and the higher the center frequency of the brainwaves, the higher the wakefulness is.

FIG. 5 indicates that the color temperature has greater effects on the wakefulness than the illuminance has. Specifically, the wakefulness tends to reduce greater when the color temperature is 3000 K than when the color temperature is 5000 K.

The user often looks down while using toilet pan 20 in the cubicle. For this reason, controller 50 causes second illumination apparatus 32 to emit light having a first color temperature lower than the color temperature of light emitted by first illumination apparatus 31 in the non-wakeup mode, thereby effectively reducing the wakefulness of the user.

On the other hand, there is no need to inhibit an increase of the wakefulness in the wakeup mode, rather, the user may better be woken up. Thus, in the wakeup mode, controller 50 sets the color temperature of the light emitted by second illumination apparatus 32 to the second color temperature higher than in the non-wakeup mode. This inhibits a reduction of the wakefulness of the user.

As described above, in the non-wakeup mode, controller 50 causes second illumination apparatus 32 to emit light having the first color temperature lower than the color temperature of light emitted by first illumination apparatus 31. In the wakeup mode, controller 50 causes second illumination apparatus 32 to emit light having the second color temperature higher than the first color temperature.

This allows cubicle unit 100 to inhibit the user from being fully awakened unnecessarily. For example, if cubicle unit 100 is provided in an aircraft, the user can have a good sleep even after returning to the cabin from the cubicle, thereby allowing the user to make the most of the air travel.

In the non-wakeup mode, controller 50, specifically, causes first illumination apparatus 31 to emit light dimmer than in the wakeup mode.

According to this, first illumination apparatus 31 also emits dim light when it is dark outside the cubicle, thereby allowing the user moved out of the cubicle to readily adapt to the dark environment outside the cubicle. Thus, a danger that the user falls down or causes a collision is reduced. Stated differently, safety is enhanced.

Figure 6:
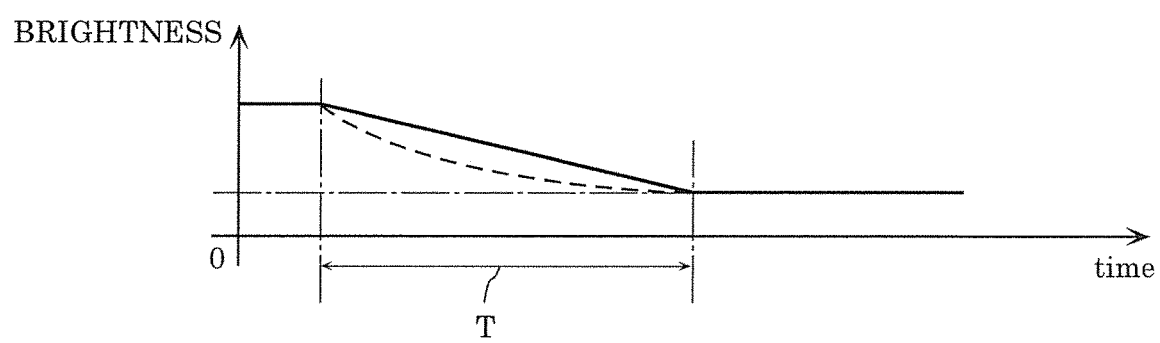
FIG. 6 is a diagram for illustrating control of dimming light, which is emitted by an illumination apparatus, over a predetermined time.

Moreover, controller 50 may further dim the light emitted by at least one of first illumination apparatus 31 and second illumination apparatus 32 over a predetermined time in the non-wakeup mode (in which second illumination apparatus 32 emits light having the first color temperature). Stated differently, controller 50 may further reduce the light output of at least one of first illumination apparatus 31 and second illumination apparatus 32 over a predetermined time in the non-wakeup mode. FIG. 6 is a diagram for illustrating control of dimming the light emitted by the illumination apparatus, over a predetermined time.

FIG. 6 shows changes in brightness of the light emitted by first illumination apparatus 31 or second illumination apparatus 32 over-time, starting at the beginning of the non-wakeup mode indicated by 0.

If the interior of the cubicle is too dark from the very beginning of the non-wakeup mode, there are dangers such as that the user collides with toilet pan 20 or basin 70. On the other hand, if the interior of the cubicle is too bright from the very beginning of the non-wakeup mode, it makes hard for the user to adapt to the dark environment outside the cubicle, as mentioned above.

Thus, after the start of the non-wakeup mode, controller 50 causes the light emitted by one of first illumination apparatus 31 and second illumination apparatus 32 to dim over predetermined time T, as illustrated in FIG. 6. Predetermined time T is, for example, five seconds or longer and less than one minute, but is not particularly limited. In doing so, a brightness in the cubicle is ensured in the early part of the non-wakeup mode, thereby enhancing safety, and the interior of the cubicle is dimmed in the end part of the non-wakeup mode, thereby allowing the user to readily adapt to the dark environment outside the cubicle.

Note that controller 50 may dim only the light emitted by first illumination apparatus 31 over a predetermined time or may dim only the light emitted by second illumination apparatus 32 over a predetermined time. Alternatively, controller 50 may dim both the light emitted by first illumination apparatus 31 and the light emitted by second illumination apparatus 32 over a predetermined time.

If controller 50 dims both the light emitted by first illumination apparatus 31 and the light emitted by second illumination apparatus 32 over a predetermined time, controller 50 may simultaneously start dimming the light emitted by first illumination apparatus 31 and the light emitted by second illumination apparatus 32, or may start dimming one of the light emitted by first illumination apparatus 31 and the light emitted by second illumination apparatus 32 earlier, in time, than the other. The timing of the start of dimming is not particularly limited. The dimming may start simultaneously with the start of the non-wakeup mode illumination control, for example.

Moreover, the light emitted by first illumination apparatus 31 and the light emitted by second illumination apparatus 32 may dim linearly as illustrated in the solid line in FIG. 6 or may dim following a curve corresponding to a reaction of photoreceptor of the user, as indicated by the dotted line in FIG. 6, for example.

Another Control Example 1

In the following, another control that is different from the illumination control set forth above is described.

Figure 7:
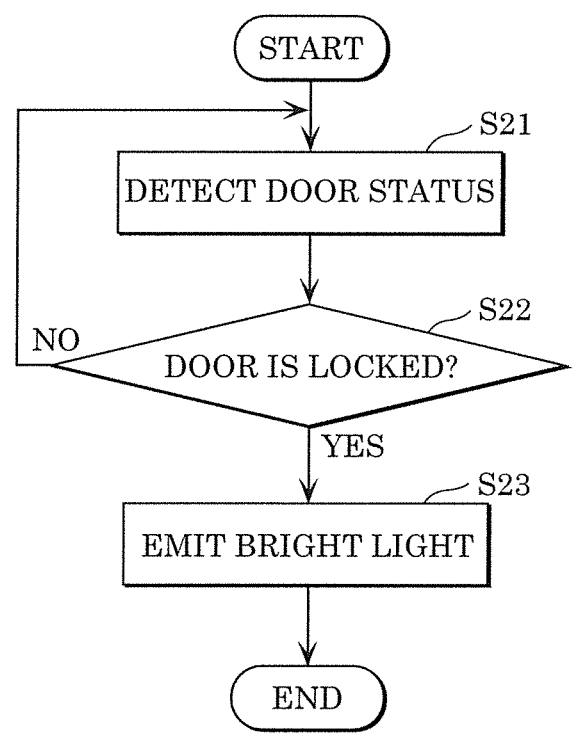
FIG. 7 is a flowchart of illumination control in response to locking of a door.

Controller 50 may determine that door 60 is locked, based on a detection by door detector 65, and cause at least one of first illumination apparatus 31 and second illumination apparatus 32 to emit brighter light than before door 60 is locked. FIG. 7 is a flowchart of such illumination control depending on locking of door 60.

Initially, door detector 65 detects a status of door 60 (S21). As described above, door detector 65, specifically, detects whether door 60 is locked, and outputs, as the detection, the first digital signal whose logic depends on whether door 60 is locked.

Controller 50 determines whether door 60 is locked, based on the detection by door detector 65 (S22). If controller 50 determines that door 60 is locked (Yes in S22), controller 50 causes at least one of first illumination apparatus 31 and second illumination apparatus 32 to emit light brighter than before door 60 is locked (S23). If door 60 is not locked (No in S22), detection of the status of door 60 continues.

Note that controller 50 may cause only first illumination apparatus 31 to emit bright light, or may cause only second illumination apparatus 32 to emit bright light. Alternatively, controller 50 may cause both first illumination apparatus 31 and second illumination apparatus 32 to emit bright light.

A period during which door 60 is not locked is considered as a period where there is no user in the cubicle, a period where there is no need to illuminate the interior of the cubicle with bright light. According to the illumination control, by controller 50, depending on locking of door 60, the light emitted by first illumination apparatus 31 and second illumination apparatus 32 in such a period can be dimmed or turned off. In other words, energy conservation of cubicle unit 100 is achieved by reducing unnecessarily light emission of first illumination apparatus 31 and second illumination apparatus 32.

Another Control Example 2

Figure 8:
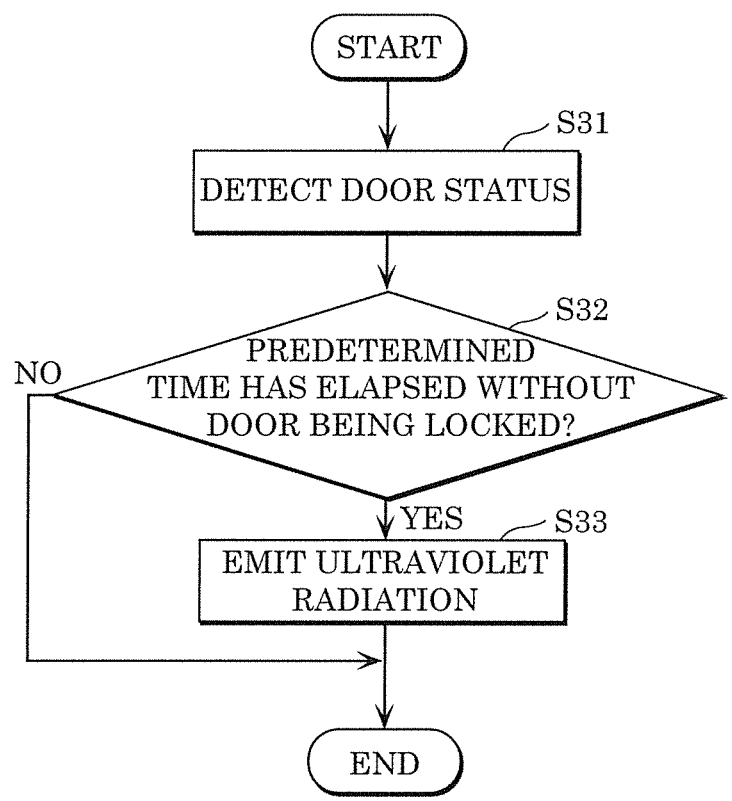
FIG. 8 is a flowchart of control of emission of ultraviolet radiation.

Controller 50 may cause UV radiator 32b to emit ultraviolet radiation if controller 50 determines that door 60 is not locked after being closed, based on a detection by door detector 65. FIG. 8 is a flowchart of such radiation control of ultraviolet radiation.

Initially, door detector 65 detects a status of door 60 (S31). As described above, door detector 65, specifically, detects whether door 60 is locked, and outputs, as the detection, the first digital signal whose logic depends on whether door 60 is locked. Door detector 65 also outputs, as the detection, the second digital signal whose logic depends on an open and closed state of door 60.

Controller 50 determines whether door 60 has remained not locked for a predetermined period since door 60 is closed, based on the detection by door detector 65 (S32). If controller 50 determines that the predetermined period has elapsed with door 60 remained not locked after being closed (Yes in S32), that is, if controller 50 determines that door 60 is not locked after being closed, controller 50 causes UV radiator 32b to emit ultraviolet radiation (S33).

On the other hand, if door 60, after being closed, is locked before an elapse of the predetermined period (No in S32), the above control is terminated. In other words, controller 50 does not allow UV radiator 32b to emit ultraviolet radiation.

UV radiator 32b emits ultraviolet radiation to disinfect (sterilize) the interior of the cubicle. On the other hand, since ultraviolet radiation is harmful, it is dangerous to cause UV radiator 32b to emit ultraviolet radiation while the user is still in the cubicle. Similarly, it is also dangerous to cause UV radiator 32b to emit ultraviolet radiation, with door 60 open.

Here, the case where door 60 is detected to be closed and not locked is a case where it is estimated that door 60 is closed with the user absent (left) in the cubicle. Since controller 50 causes UV radiator 32b to emit ultraviolet radiation in such a case, the interior of the cubicle can be disinfected in safety. Moreover, since controller 50 requires an elapse of the predetermined period to allow the emission of ultraviolet radiation, ultraviolet radiation is inhibited from being emitted inadvertently when the user is in the cubicle, thereby further enhancing the safety.

[Variations of Placement of Second Illumination Apparatus]

Figure 9A:
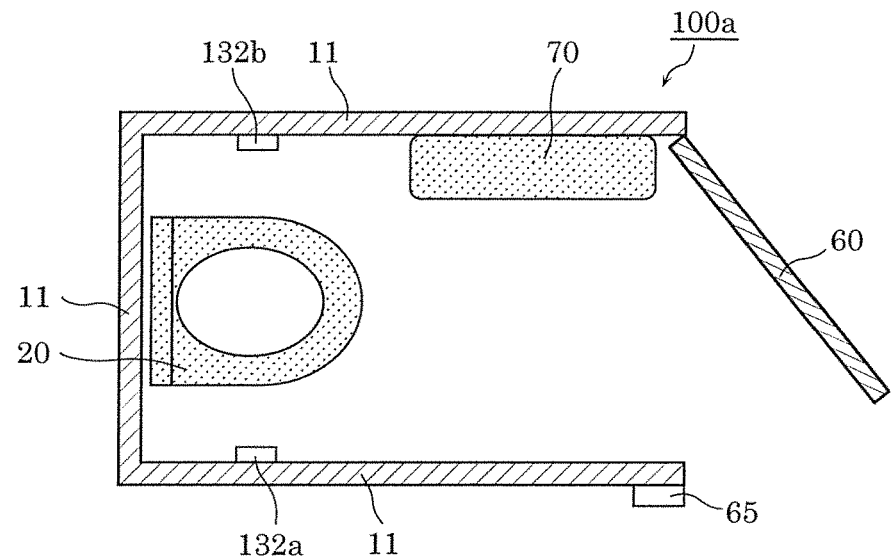
FIG. 9A is a diagram illustrating an internal construction of a cubicle unit according to Variation 1 when viewed from the top.
Figure 9B:
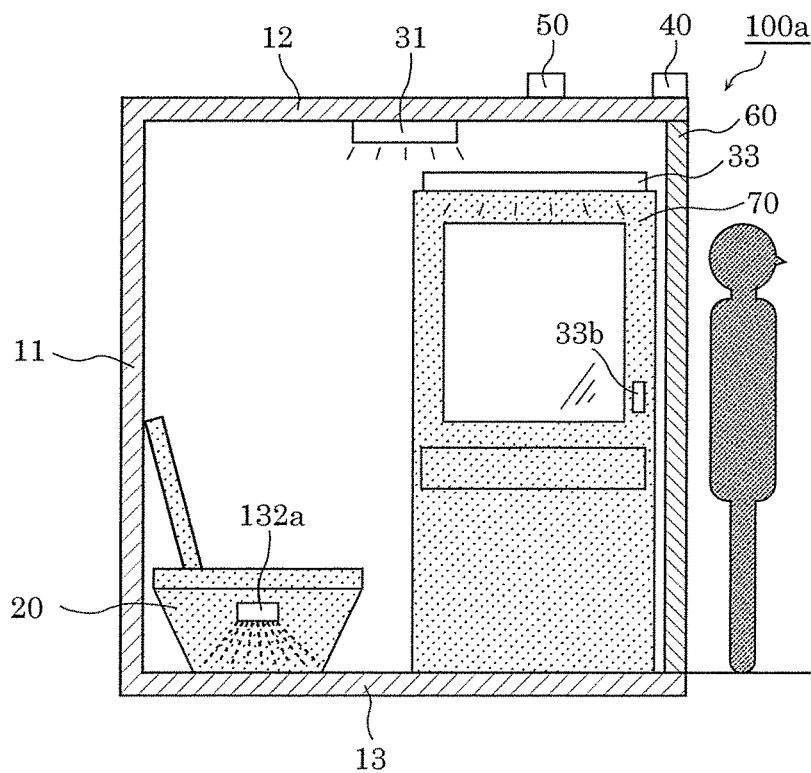
FIG. 9B is a diagram illustrating the internal construction of the cubicle unit according to Variation 1 when viewed from the side.

The placement of the second illumination apparatus (second illumination apparatus 32) described in the above embodiment is by way of example, and is not particularly limited. In the following, variations of the placement of the second illumination apparatus are described. FIG. 9A is a diagram illustrating an internal construction of a cubicle unit according to Variation 1 of the embodiment when viewed from the top. FIG. 9B is a diagram illustrating the internal construction of the cubicle unit according to Variation 1 when viewed from the side.

Cubicle unit 100a illustrated in FIGS. 9A and 9B includes second illumination apparatus 132a and second illumination apparatus 132b. Second illumination apparatus 132a and second illumination apparatus 132b are placed on sidewalls 11 that are on both sides of toilet pan 20, and are controlled collectively by controller 50 similar to the control described above with respect to second illumination apparatus 32. Second illumination apparatus 132a and second illumination apparatus 132b are placed in a manner to have toilet pan 20 therebetween in the horizontal direction. Second illumination apparatus 132a and second illumination apparatus 132b are placed at positions lower than the top end of toilet pan 20.

Figure 10A:
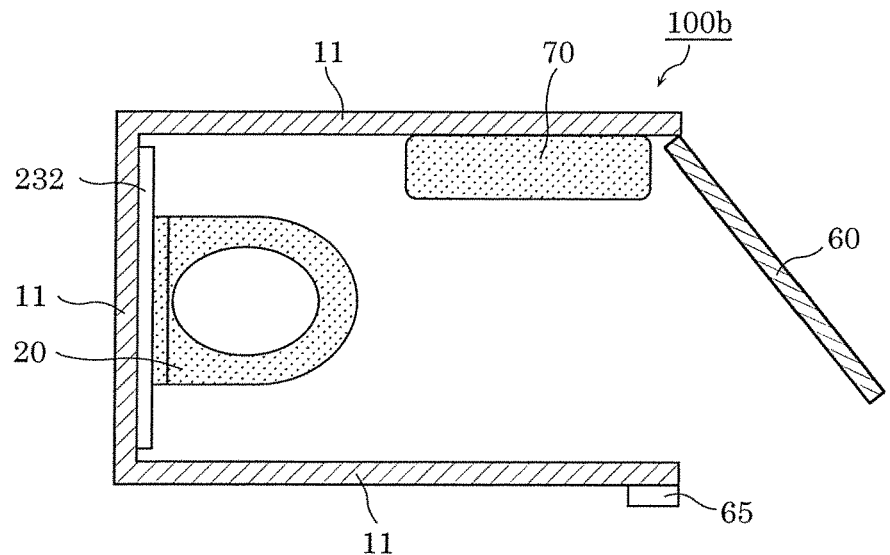
FIG. 10A is a diagram illustrating an internal construction of a cubicle unit according to Variation 2 when viewed from the top.
Figure 10B:
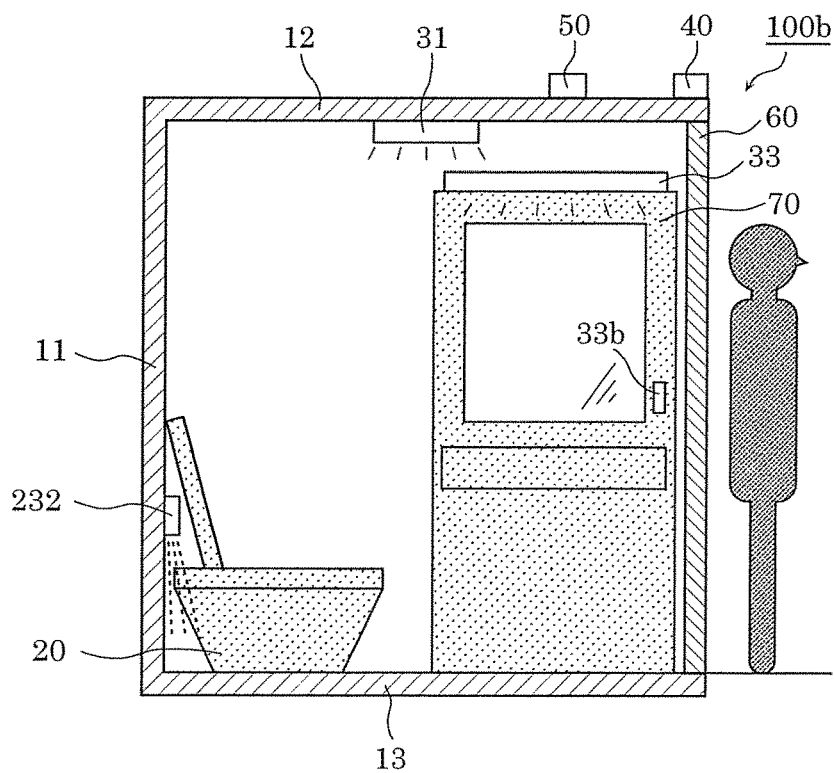
FIG. 10B is a diagram illustrating the internal construction of the cubicle unit according to Variation 2 when viewed from the side.

FIG. 10A is a diagram illustrating an internal construction of a cubicle unit according to Variation 2 of the embodiment when viewed from the top. FIG. 10B is a diagram illustrating the internal construction of the cubicle unit according to Variation 2 when viewed from the side.

Cubicle unit 100b illustrated in FIGS. 10A and 10B includes second illumination apparatus 232 in an elongated shape. Second illumination apparatus 232 is placed on one of sidewalls 11 that is located behind toilet pan 20 in a manner that the lengthwise direction of second illumination apparatus 232 is along the horizontal direction. Second illumination apparatus 232 is placed at a position lower than the top end of toilet pan 20.

Figure 11A:
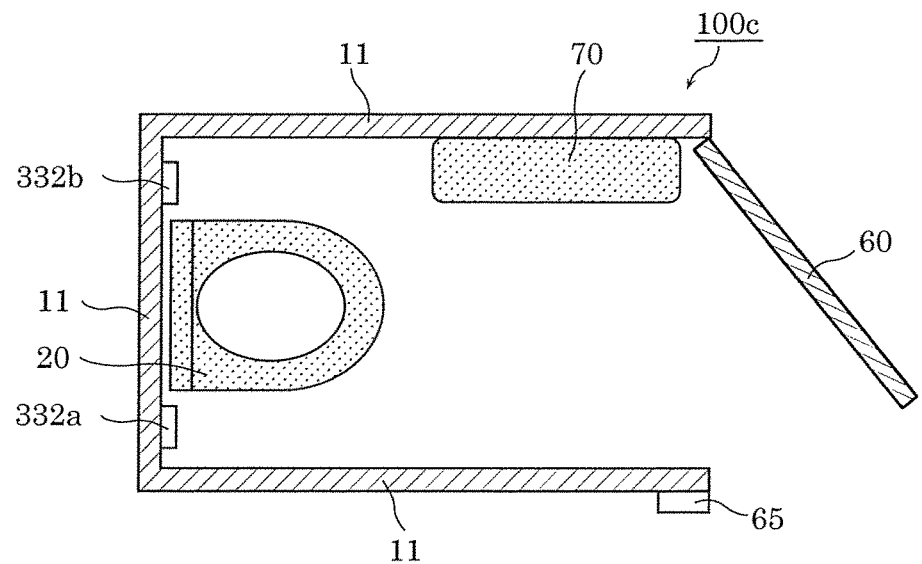
FIG. 11A is a diagram illustrating an internal construction of a cubicle unit according to Variation 3 when viewed from the top.
Figure 11B:
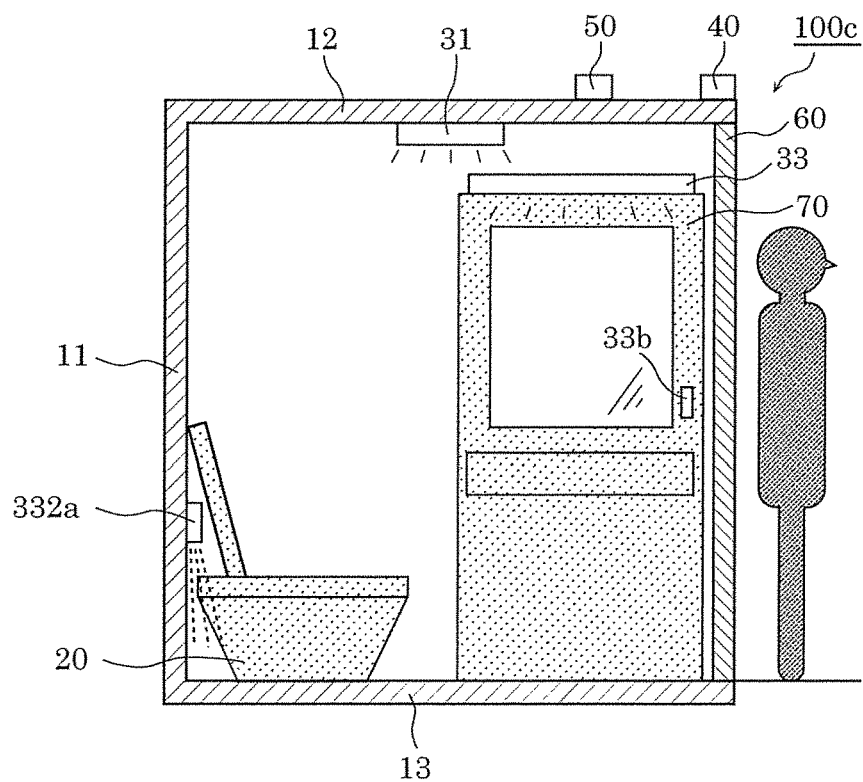
FIG. 11B is a diagram illustrating the internal construction of the cubicle unit according to Variation 3 when viewed from the side.

FIG. 11A is a diagram illustrating an internal construction of a cubicle unit according to Variation 3 of the embodiment when viewed from the top. FIG. 11B is a diagram illustrating the internal construction of the cubicle unit according to Variation 3 when viewed from the side.

Cubicle unit 100c illustrated in FIGS. 11A and 11B includes second illumination apparatus 332a and second illumination apparatus 332b. Second illumination apparatus 332a and second illumination apparatus 332b are placed on one of sidewalls 11 that is located behind toilet pan 20. Second illumination apparatus 332a and second illumination apparatus 332b are placed apart from each other in the horizontal direction, and controlled collectively by controller 50 again, similar to second illumination apparatus 32 described above. Second illumination apparatus 332a and second illumination apparatus 332b are placed at positions lower than the top end of toilet pan 20.

Cubicle unit 100a, cubicle unit 100b, and cubicle unit 100c described above also inhibit the user from being fully awakened unnecessarily, by controller 50 performing the illumination control described above.

[Summary]

As described above, cubicle unit 100 includes: sidewalls 11, ceiling 12, and flooring 13 which form a cubicle; toilet pan 20 placed in the cubicle; and first illumination apparatus 31 which emits light to illuminate an interior of the cubicle, first illumination apparatus 31 being placed on ceiling 12 or one of sidewalls 11. Cubicle unit 100 also includes: second illumination apparatus 32 which emits light to illuminate a floor surface of the cubicle, the floor surface being part of flooring 13, second illumination apparatus 32 being placed at a position lower than a top end of toilet pan 20 in the cubicle; sensor 40 which senses a brightness outside the cubicle; and controller 50. When the brightness sensed by sensor 40 is a predetermined brightness or less, controller 50 causes second illumination apparatus 32 to emit light having a first color temperature lower than a color temperature of light emitted by first illumination apparatus 31. When the brightness sensed by sensor 40 is greater than the predetermined brightness, controller 50 causes second illumination apparatus 32 to emit light having a second color temperature higher than the first color temperature.

This allows second illumination apparatus 32 to emit light having the first color temperature which reduces the wakefulness of the user when it is dark outside cubicle unit 100, thereby inhibiting the user from being fully awakened unnecessarily. For example, if cubicle unit 100 is provided in an aircraft, the user can have a good sleep even after returning to the cabin from the cubicle, thereby allowing the user to make the most of the air travel.

Moreover, if the brightness sensed by sensor 40 is the predetermined brightness or less, controller 50 may further cause first illumination apparatus 31 to emit light dimmer than when the brightness sensed by sensor 40 is greater than the predetermined brightness. Stated differently, controller 50 may further cause first illumination apparatus 31 to emit light having a first brightness when the brightness sensed by sensor 40 is the predetermined brightness or less, and cause first illumination apparatus 31 to emit light having a second brightness greater than the first brightness when the brightness sensed by sensor 40 is greater than the predetermined brightness.

This causes first illumination apparatus 31 to emit dim light when it is dark outside the cubicle, thereby allowing the user moved out of the cubicle to readily adapt to the dark environment outside the cubicle. Thus, a danger that the user falls down or causes a collision is reduced. Stated differently, the safety is enhanced.

Moreover, cubicle unit 100 may further include door 60 for allowing a user to enter and exit the cubicle, door 60 being lockable from inside the cubicle by the user; and door detector 65 which detects whether door 60 is locked. Door detector 65 is an example of the lock detector. At this time, controller 50 may determine that door 60 is locked, based on a detection by door detector 65, and cause at least one of first illumination apparatus 31 and second illumination apparatus 32 to emit light brighter than before door 60 is locked.

This reduces unnecessary light emission of first illumination apparatus 31 and second illumination apparatus 32 during a period where no one is expected to be in the cubicle, thereby achieving energy conservation of cubicle unit 100.

Moreover, while causing second illumination apparatus 32 to emit the light having the first color temperature, controller 50 may further cause the light emitted by at least one of first illumination apparatus 31 and second illumination apparatus 32 to dim over a predetermined time.

According to this, a brightness in the cubicle is ensured in the early part of second illumination apparatus 32 emitting light having the first color temperature, thereby enhancing the safety, and the interior of the cubicle is dimmed in the end part, thereby allowing the user to readily adapt to the dark environment outside the cubicle.

Moreover, cubicle unit 100 may further include door detector 65 which detects opening and closing of door 60, and second illumination apparatus 32 may further include UV radiator 32b which emits ultraviolet radiation. Door detector 65 is an example of the opening and closing detector. At this time, controller 50 may further cause UV radiator 32b to emit ultraviolet radiation if controller 50 determines that door 60 is not locked after being closed, based on a detection by door detector 65.

This causes emission of ultraviolet radiation when it is estimated that door 60 is closed without a user present in the cubicle, thereby disinfecting the interior of the cubicle in safety.

Moreover, cubicle unit 100 may further include basin 70 placed in the cubicle; and third illumination apparatus 33 which emits light to illuminate the user at basin 70, wherein emission of the light by third illumination apparatus 33 is controlled independently of first illumination apparatus 31 and second illumination apparatus 32.

This allows the user of basin 70 to freely use third illumination apparatus 33, irrespective of the illumination statuses of first illumination apparatus 31 and second illumination apparatus 32.

Moreover, third illumination apparatus 33 may include light emitter 33a which is configured to emit light in a plurality of illumination modes and receiver 33b which receives a selection from among the plurality of illumination modes.

This allows the user to select an illumination mode of third illumination apparatus 33.

Moreover, third illumination apparatus 33 may have a color rendering property higher than first illumination apparatus 31.

This can provide the user of basin 70 with high color reproduction.

Moreover, cubicle unit 100 may be placed in a transportation vehicle, and sensor 40 may sense the brightness outside the cubicle which is a brightness in the transportation vehicle.

This allows cubicle unit 100 to perform the illumination control, based on the brightness outside the cubicle which is a brightness in the transportation vehicle.

Moreover, an illumination control method according to the above embodiment is a method for controlling illumination in cubicle unit 100. The illumination control method includes: sensing a brightness outside the cubicle; and causing, when the brightness sensed is a predetermined brightness or less, second illumination apparatus 32 to emit light having a first color temperature lower than a color temperature of light emitted by first illumination apparatus 31. The illumination control method also includes causing, when the brightness sensed is greater than the predetermined brightness, second illumination apparatus 32 to emit light having a second color temperature higher than the first color temperature. The illumination control method is executed by, for example, a control apparatus or the like which includes sensor 40 and controller 50 (a processor).

This allows, when it is dark outside cubicle unit 100, second illumination apparatus 32 to emit light having the first color temperature which facilitates a reduction of the wakefulness of the user, thereby inhibiting the user from being fully awakened unnecessarily. For example, if cubicle unit 100 is provided in an aircraft, the user can have a good sleep even after returning to the cabin from the cubicle.

Other Embodiments

While the cubicle unit and illumination control method according to the embodiment have been described above, the present disclosure is not limited to the above embodiment.

For example, while the light emitter described in the above embodiment is configured of an LED, such a configuration is one example. A lamp tube, a metal halide lamp, a sodium lamp, a halogen lamp, a Xenon lamp, a neon tube, etc. may be used as the light emitter. An inorganic electro-luminescence, an organic electro-luminescence, a chemiluminescence, a semiconductor laser, etc. may also be used as the light emitter. Moreover, the light emitter may emit light having a desired color, using a spectral filter, for example. The light emitter may be configured in any way to an extent that can allow the controls (dimming control or color control) required for the illumination control.

Moreover, generic and specific aspects of the present disclosure may be implemented in a system, a method, an integrated circuit, a computer program, or a computer-readable recording medium such as a CD-ROM, or any combination of systems, methods, integrated circuits, computer programs, or computer-readable recording media such as CD-ROM. For example, the present disclosure may be implemented in the illumination control method, a program for causing a computer to execute the illumination control method, or in the controller (control apparatus) according to the above embodiments.

Figure 12:
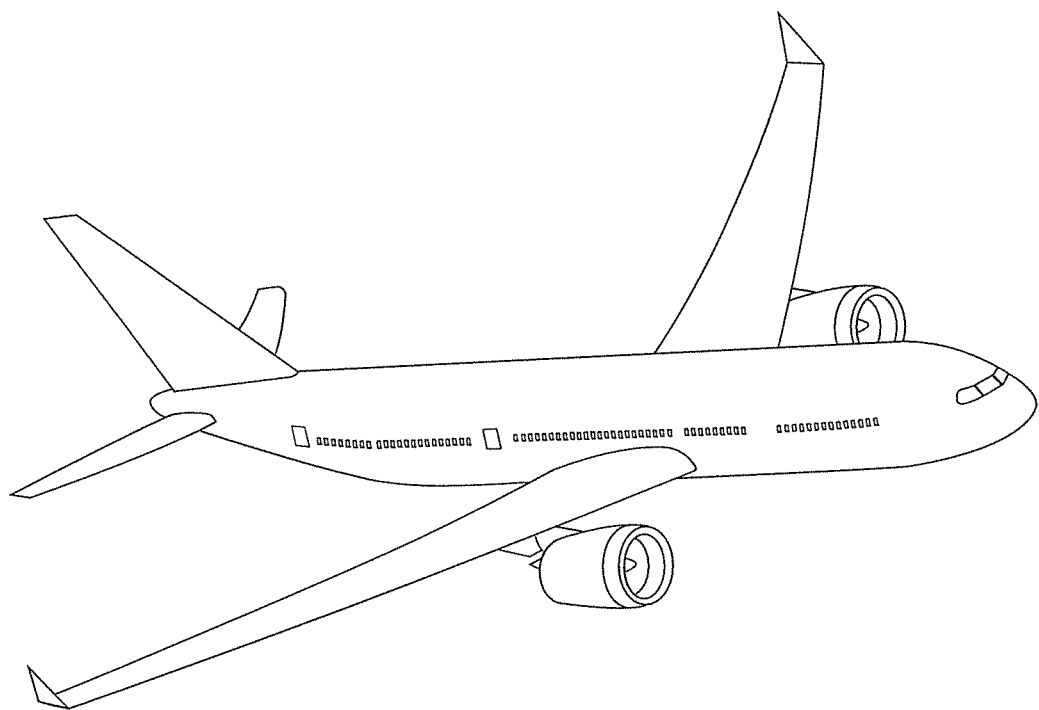
FIG. 12 is an external view of an aircraft.

Moreover, the present disclosure may be implemented in a transportation vehicle which includes: the cubicle unit according to the embodiments described above; and a transport body inside which the cubicle unit is located. Examples of the transportation vehicle include an aircraft as illustrated in FIG. 12. However, the transportation vehicle may be any other means of transportation such as a train and a ship. FIG. 12 is an external view of an aircraft.

Moreover, all or some of the components in the above embodiments, such as the controller, may be configured with dedicated hardware or may be implemented by executing a software program suitable for the component. Each component may be implemented by a program execution unit, such as a CPU or processor, loading and executing the software program stored in a recording medium such as a hard disk or a semiconductor memory.

Moreover, in the above embodiments, processing performed by a particular processing unit may be performed by another processing unit. The order of processes may be changed or the processes may be performed in parallel.

In other instances, various modifications to the exemplary embodiments according to the present disclosure described above that may be conceived by a person skilled in the art and embodiments implemented in any combination of the components and functions shown in the exemplary embodiments are also included within the scope of the present disclosure, without departing from the spirit of the present disclosure.

What is claimed is:
1. A cubicle unit comprising:
sidewalls, ceiling, and flooring which form a cubicle;
a toilet pan placed in the cubicle;
a first illumination apparatus which emits light to illuminate an interior of the cubicle, the first illumination apparatus being placed on the ceiling or one of the sidewalls;
a second illumination apparatus which emits light to illuminate a floor surface of the cubicle, the floor surface being part of the flooring, the second illumination apparatus being placed at a position lower than a top end of the toilet pan in the cubicle;
a sensor which senses a brightness outside the cubicle; and
a controller which
(i) causes, when the brightness sensed by the sensor is a predetermined brightness or less, the second illumination apparatus to emit light having a first color temperature lower than a color temperature of light emitted by the first illumination apparatus, and
(ii) causes, when the brightness sensed by the sensor is greater than the predetermined brightness, the sec- ond illumination apparatus to emit light having a second color temperature higher than the first color temperature.

2. The cubicle unit according to claim 1, wherein
the controller further causes the first illumination apparatus to emit light having a first brightness when the brightness sensed by the sensor is the predetermined brightness or less, and causes the first illumination apparatus to emit light having a second brightness greater than the first brightness when the brightness sensed by the sensor is greater than the predetermined brightness.

3. The cubicle unit according to claim 1, further comprising:
a door for allowing a user to enter and exit the cubicle, the door being lockable from inside the cubicle by the user; and
a lock detector which detects whether the door is locked, wherein
the controller determines that the door is locked, based on a detection by the lock detector, and causes at least one of the first illumination apparatus and the second illumination apparatus to emit light brighter than before the door is locked.

4. The cubicle unit according to claim 3, further comprising:
an opening and closing detector which detects opening and closing of the door, wherein
the second illumination apparatus further includes a radiator which emits ultraviolet radiation, and
the controller further causes the radiator to emit ultraviolet radiation when the controller determines that the door is not locked after being closed, based on a detection by the opening and closing detector and a detection by the lock detector.

5. The cubicle unit according to claim 1, wherein
while causing the second illumination apparatus to emit the light having the first color temperature, the controller further causes the light emitted by at least one of the first illumination apparatus and the second illumination apparatus to dim over a predetermined time.

6. The cubicle unit according to claim 1, further comprising:
a basin placed in the cubicle; and
a third illumination apparatus which emits light to illuminate the user at the basin, wherein emission of the light by the third illumination apparatus is controlled independently of the first illumination apparatus and the second illumination apparatus.

7. The cubicle unit according to claim 6, wherein
the third illumination apparatus includes a light emitter which is configured to emit light in a plurality of illumination modes, and a receiver which receives a selection from among the plurality of illumination modes.

8. The cubicle unit according to claim 6, wherein
the third illumination apparatus has a color rendering property higher than the first illumination apparatus.

9. The cubicle unit according to claim 1, wherein
the cubicle unit is placed in a transportation vehicle, and
the sensor senses the brightness outside the cubicle which is a brightness in the transportation vehicle.

10. A transportation vehicle comprising:
the cubicle unit according to claim 1; and
a transport body inside which the cubicle unit is located.

11. A method for controlling illumination in a cubicle unit including:
sidewalls, ceiling, and flooring which form a cubicle;
a toilet pan placed in the cubicle;
a first illumination apparatus which emits light to illuminate an interior of the cubicle, the first illumination apparatus being placed on the ceiling or one of the sidewalls; and
a second illumination apparatus which emits light to illuminate a floor surface of the cubicle, the floor surface being part of the flooring, the second illumination apparatus being placed at a position lower than a top end of the toilet pan in the cubicle,
the method comprising:
sensing a brightness outside the cubicle;
causing, when the brightness sensed is a predetermined brightness or less, the second illumination apparatus to emit light having a first color temperature lower than a color temperature of light emitted by the first illumination apparatus; and
causing, when the brightness sensed is greater than the predetermined brightness, the second illumination apparatus to emit light having a second color temperature higher than the first color temperature.

* * * * *